United States Patent [19]

Bertocchio

[11] Patent Number: 5,608,129
[45] Date of Patent: Mar. 4, 1997

[54] PROCESS FOR THE PURIFICATION OF DIFLUOROMETHANE

[75] Inventor: Rene Bertocchio, Vourles Par Vernaison, France

[73] Assignee: Elf Atochem S.A., Puteaux, France

[21] Appl. No.: 534,263

[22] Filed: Sep. 26, 1995

[30] Foreign Application Priority Data

Sep. 26, 1994 [FR] France .................... 94 11449

[51] Int. Cl.$^6$ .............. C07C 17/38; C07C 17/389; B01J 20/34; B01J 38/64
[52] U.S. Cl. .............................. 570/179; 502/25
[58] Field of Search .............. 570/179; 502/25

[56] References Cited

U.S. PATENT DOCUMENTS

| | | | |
|---|---|---|---|
| 3,215,747 | 11/1965 | Fainberg et al. | 570/179 |
| 4,558,022 | 12/1985 | Farmerie | 502/25 |
| 4,906,796 | 3/1990 | Yates | 570/179 |
| 5,001,094 | 3/1991 | Chang et al. | 502/25 |
| 5,210,342 | 5/1993 | Moore | 570/179 |

FOREIGN PATENT DOCUMENTS

| | | | |
|---|---|---|---|
| 0508630 | 10/1993 | European Pat. Off. . | |
| B-1206424 | 11/1993 | Germany . | |
| 3223219 | 10/1991 | Japan | 570/179 |
| 9212791 | 8/1992 | WIPO | 502/25 |

Primary Examiner—Joseph E. Evans
Attorney, Agent, or Firm—Spencer & Frank

[57] ABSTRACT

To remove the traces of chlorofluoromethane present in a difluoromethane, the difluoromethane to be purified is passed over a 13X molecular sieve at a temperature of at least 60° C.

The sieve can be regenerated by washing with the aid of a solution of sodium or potassium carbonate and heating to high temperature under inert atmosphere or in vacuum.

7 Claims, No Drawings

PROCESS FOR THE PURIFICATION OF DIFLUOROMETHANE

FIELD OF INVENTION

The present invention relates to the field of fluorohydrocarbons and its subject is more particularly the purification of difluoromethane ($CH_2F_2$) containing traces of chlorofluoromethane ($CH_2ClF$).

BACKGROUND OF THE INVENTION

Difluoromethane (known in the trade under the designation F32) is one of the possible substitutes for chlorofluorocarbons (CFCs) which are dealt with by the Montreal Protocol and is intended to replace more particularly chloropentafluoroethane (F115), the action of which on ozone is accompanied by a powerful contribution to the greenhouse effect.

F32 can be obtained by fluorination of methylene chloride ($CH_2Cl_2$) by means of HF in the presence of a catalyst or by hydrogenolysis of dichlorodifluoromethane (F12) or of chlorodifluoromethane (F22) or else by decomposition, in the presence of HF, of alpha-fluoroethers under the action of Lewis acids.

However, fluorination processes exhibit the disadvantage of involving the formation, as intermediate, of chlorofluoromethane (F31), a toxic compound which, according to the classification of the IARC (International Agency for Research on Cancer) is classified in category IIB (possibly cancerogenic to man) and the residual concentration of which it is appropriate to lower to about one ppm. Despite the difference in volatility between F31 (b.p. $-9.1°$ C.) and F32 (b.p.: $-51.7°$ C.), this objective is difficult to obtain by distillation and therefore requires the development of a highly efficient purification process. Small quantities of F31 may also be present in an F32 manufactured by hydrogenolysis of F12 or of F22.

To lower the F31 content in an F32, patent application EP 508 630 describes a process consisting in placing the F32 to be purified in contact with an activated carbon. The selectivity is not very high and the methylene chloride or the dichlorodifluoromethane is adsorbed in the same proportions as F31, thus limiting the capacity of the adsorbent. It is known, furthermore, that the properties of an activated carbon depend greatly on its method of preparation and on the raw material employed; the effectiveness of an activated carbon and above all its selectivity are therefore liable to variations depending on the source of the batches.

The use of molecular sieves for the purification of fluorohydrocarbons is already known. The purification treatments are usually performed at ambient temperature or thereabouts. Temperatures lower than ambient temperature are sometimes recommended, as in U.S. Pat. No. 2,917,556, claiming the use of 5A, 10X or 13X sieves for the removal of vinyl fluoride from vinylidene fluoride or in patent application JP 5-70381, which recommends a temperature region ranging from $-30°$ to $+30°$ C. for removing HFC 365 ($C_4F_5H_5$) and the corresponding olefins ($C_4F_4H_4$) from a crude 1,1-dichloro-1-fluoroethane (F141b) by treatment on 13X molecular sieve.

With zeolites A or a natural sieve such as chabazite, patent application EP 503 796 recommends temperatures of between $+10°$ and $+100°$ C. for removing any trace of 1-chloro-2,2-difluoroethylene (F1122) from 1,1,1,2-tetrafluoroethane (F134a), but the treatments are in practice performed at 40° C.

In the purification of F 134a, but for the removal of 1,1,2,2-tetrafluoroethane (F134), patent application JP 3-72437 employs zeolites which have a pore diameter of between 5 and 7 Å over a temperature region of between 0° and 70° C.

These sieves are generally regenerated by heating to 200°–350° C. under a stream of air or nitrogen, by heating under reduced pressure or else by displacement of the adsorbed products with water and reactivation at high temperature, as indicated in U.S. Pat. No. 2,917,556. These regeneration processes, well known to a person skilled in the art, appear in most of the technical data sheets supplied by the manufacturers of molecular sieves.

Although patent DE 1 218 998 mentions that 13X molecular sieves can work at a relatively high temperature, none of the abovementioned documents allows any change or increase in selectivity whatever to be expected when the temperature of treatment is raised.

DESCRIPTION OF THE INVENTION

It has now been found that 13X molecular sieves enable F31 to be completely removed from F32, on condition that the treatment is performed at a temperature of at least 60° C.

It has also been found that, in the case of this purification of F32 on 13X sieve, conventional regeneration methods are not suitable, but that the spent 13X sieve can be restored to its full effectiveness by being washed with a solution of sodium or potassium carbonate before being reactivated by heating under inert atmosphere or in vacuum.

The subject of the invention is therefore a process for the purification of an F32 containing traces of F31, characterized in that a gaseous stream of the F32 to be purified is passed over a 13X molecular sieve at a temperature of at least 60° C. and, preferably, higher than 75° C.

Another subject of the invention is such a process of purification in which, after use, the 13X sieve is regenerated by washing by means of a solution of sodium or potassium carbonate and heating to high temperature under inert atmosphere or in vacuum.

13X molecular sieves form part of the class of synthetic zeolites of the X/Y type and have a crystalline structure in the form of cubo-octahedra containing cavities which are accessible via pores of an effective opening diameter of 10 Å; their specific surface is of the order of 800 to 1000 m²/g and, in the sodium form, they correspond to the general formula:

$$Na_{86}[(AlO_2)_{86}(SiO_2)_{106}]276H_2O$$

These sieves, which can also be employed in the potassium form, are obtained by hydrothermal crystallization of gels resulting from the mixing, in well-defined proportions, of alkaline aqueous solutions of silicates and of aluminates (R. Belabbes and J. M. Vergnaud, Chimie et Industrie, vol. 104, June 1971, pages 1407 et seq.).

The hourly space velocity of the gaseous stream of F32 to be purified on the particles of 13X molecular sieve, arranged as a fixed or fluid bed, may vary within wide limits. It is generally between 20 and 2400 $h^{-1}$, preferably between 40 and 250 $h^{-1}$.

Placing the F32 to be purified in contact with the 13X molecular sieve may be performed at atmospheric pressure or at a higher pressure that can range up to 30 bars.

The process according to the invention may be applied to the purification of an F32 containing up to 5000 ppm of F31, and more particularly up to 2000 ppm.

The regeneration of the sieve must be performed at a temperature not exceeding 550° C. and is advantageously conducted as follows. At the end of the purification cycle the sieve is desorbed at 150°–250° C. under a stream of nitrogen or, better, in vacuum, so as to recover the F32 adsorbed on the zeolite. The sieve is then placed in contact with an aqueous solution containing 1 to 5% by weight of sodium or potassium carbonate for a period which may range from 1 to 12 hours, and is then separated, rinsed with distilled water and dried before reactivation at 200°–250° C. under inert atmosphere (nitrogen, helium, argon) or in vacuum.

The desorption and reactivation stages may be performed in a vacuum which, depending on the available condensation device, may range from a few tens of kilopascals to several hundred pascals. In industrial practice the work is generally done in a vacuum of between a few tens of kilopascals and 6000 pascals.

EXAMPLES

The following examples illustrate the invention without limiting it. The ppm values shown are expressed as weight and determined by vapour phase chromatography (VPC).

EXAMPLE 1 a) 26 g of a 13X molecular sieve in the form of 1.6-mm extrudates (Siliporite® G5 marketed by CECA), activated beforehand at 250° C. for 2 hours under a stream of nitrogen were arranged in a tube 50 cm in height and 10 mm in internal diameter, provided with a heating jacket, and then a gaseous stream of F32 containing 100 ppm of F31 was passed through at ambient temperature and at a flow rate of 5 l/h.

After 7 hours' operation, VPC analysis of a sample of F32 taken at the exit of the tube showed that its F31 content fell only to 93 ppm.

b) The preceding test was repeated, but with the treatment being performed at 80° C. After 7 hours' operation, the residual F31 concentration was lower than 1 ppm (detection limit of the VPC analysis method).

EXAMPLES 2 to 4

(Comparative)

The tests of Example 1 were repeated, but with the 13X molecular sieve being replaced with 27 g of 5A molecular sieve marketed by CECA (Example 2) or with 30.8 g of acidic mordenite marketed by Ventron GmbH (Example 3) or else with 16.2 g of Norit NC activated carbon as 0.8-mm extrudates (Example 4).

The results of these tests are listed together in the following table:

|  | COMPARATIVE EXAMPLE No. | | | | | |
|---|---|---|---|---|---|---|
|  | 2 | | 3 | | 4 | |
| Temperature of treatment (°C.) | 25 | 78 | 25 | 80* | 25 | 80* |
| F31 content (ppm) at the tube exit | 100 | 62 | 88 | 100 | 47 | 107 |

*test made without renewing the charge employed at 25° C.

EXAMPLE 5

By operating as in Example 1 with 26 g of a 33X molecular sieve prepared with an iron-free binder and activated in the same conditions, tests were carried out at ambient temperature, at 68° C. and at 80° C. on the same single batch of F32 containing 100 ppm of F31. The following results were obtained:

| Temperature of treatment | F31 content at the pipe exit (ppm) |
|---|---|
| 25° C. | 100 |
| 68° C. | 30 (15 if the flow rate is reduced to 3 l/h instead of 5 l/h) |
| 80° C. | <1 |

EXAMPLE 6

51.9 g of a Union Carbide 13X sieve, conditioned in the form of extrudates 1.6 mm in diameter and activated beforehand under nitrogen at 250° C. were placed in a stainless steel tube 14 mm in internal diameter and 50 cm in height, provided with a heating jacket, and then a batch of F32 containing 250 ppm of F31 was circulated therein continuously at a flow rate of 9.8 l/h and at a temperature of 80° C. The F31 content at the exit of the tube was checked by taking samples at regular intervals. The following results were obtained:

| Cumulative operating period (hours) | Residual F31 content (ppm) |
|---|---|
| 7 | <1 |
| 14 | <1 |
| 22 | <1 |
| 38 | <1 |
| 46 | <1 |
| 62 | <1 |
| 78 | <1 |
| 81 | <1 |
| 84 | 2 |

EXAMPLE 7 a) The same tube as in Example 1 was filled with 24.4 g of Union Carbide 13X molecular sieve, activated as previously, and a stream of F32 containing 100 ppm of F31 was circulated therein at a flow rate of 5 l/h.

After 90 minutes a sample of the treated gas was taken at the exit of the tube and the temperature was raised to 45° C. for a new treatment period of 0 minutes, at the end of which the concentration of F31 was checked again. When this procedure was continued using successive plateaus up to a temperature of 125° C., the following results were obtained:

| Temperature of treatment (°C.) | Residual F31 content (ppm) |
|---|---|
| 45 | 70 |
| 60 | 35 |
| 80 | <1 |
| 100 | <1 |
| 125 | <1 | b) The operation was carried out as above with a new charge of 23.4 g of Union Carbide 13X sieve, but starting from a temperature of 125° C. and coming down to ambient temperature using successive plateaus of 90-minute duration.

The following results were obtained by employing an F32 containing 56 ppm of F31 and a flow rate of 5 l/h:

| Temperature of treatment (°C.) | Residual F31 content (ppm) |
|---|---|
| 125 | <1 |
| 100 | <1 |
| 80 | <1 |
| 60 | 8 |
| ambient | 44 |

EXAMPLE 8

49.7 g of Siliporite® G5 sieve (Ceca) were activated at 250° C. under nitrogen purging and were placed in the stainless steel tube employed in Example 6.

A batch of F32 containing 1605 ppm of F31 was circulated therein continuously at a flow rate of 4 l/h, the temperature of the sieve being maintained at 80° C. by circulating a thermostated fluid in the jacket.

The F31 content at the exit of the tube was checked by taking samples at regular intervals. The break-through point (final F31 concentration >1 ppm) appeared after 70 hours' operation, which corresponds to a capacity of 2.6% relative to the weight of the sieve introduced.

| Cumulative operating period (hours) | Residual F31 content (ppm) |
|---|---|
| 1 | <1 |
| 24 | <1 |
| 66 | <1 |
| 69 | <1 |
| 73 | 4 |
| 74.5 | 6 |

EXAMPLES 9 to 12

Each example was carried out in the same tube as in Example 6, in which a new charge (35 to 40 g) of Union Carbide 13X sieve, activated beforehand at 250° C. in vacuum (133 Pa) for 2 hours, was placed each time.

In the case of Example 12 the sieve was additionally subjected in situ to heating to 150° C. in vacuum (133 Pa) for 20 minutes, to prevent any risk of moisture uptake when it was being handled. In addition, the crude F32 was dried over a bed of 3 Å molecular sieve.

Batches of F32 containing between 1100 and 2250 ppm of F31 were circulated continuously over each charge of 13X sieve and the influence of the temperature of treatment on the capacity at break-through was determined. The results are listed in the following table.

| EXAMPLE No. | TEMPERATURE OF TREATMENT (°C.) | SIEVE WEIGHT (g) | INITIAL F31 CONCENTRATION (ppm) | CAPACITY AT BREAK-THROUGH [F31] >1 ppm |
|---|---|---|---|---|
| 9 | 80 | 39.2 | 1100 | 3.26% |
| 10 | 100 | 39.2 | 2250 | 4.26% |
| 11 | 125 | 39.5 | 2070 | 2.59% |
| 12 | 100 | 35.6 | 2050 | 4.80% |

EXAMPLE 13

(Comparative)

The spent charges from Examples 9, 10 and 12 were purged with a stream of nitrogen at ambient temperature and then desorbed at 250° C. in vacuum (133 Pa) for 2 hours and were combined to form a batch of sieve to be regenerated.

50 g of this batch were suspended for 4 hours in one liter of distilled water and were then drained and dried up to 120° C. in the oven before being reactivated at 250° C. in vacuo (133 Pa).

42 g of this sieve were placed in the same tube as in Example 6 and a stream of crude F32 containing 2050 ppm of F31 was circulated therein at 80° C. at a flow rate of 3.6 l/h.

After 19 hours the residual F31 concentration already reached 4 ppm and increased rapidly subsequently. The calculated capacity at the break-through point does not exceed 0.8%.

EXAMPLE 14

50 g of the same batch as in Example 13, made up by combining the spent charges resulting from Examples 9, 10 and 12 and from their desorption at 250° C. in vacuum, were suspended in 500 ml of an aqueous solution containing 2% of sodium carbonate and were stirred slowly for 4 hours. After draining, the charge was rinsed with two 250-ml portions of distilled water and was then dried and finally reactivated by heating to 250° C. in vacuum (133 Pa) for 2 hours.

35.3 g of the sieve regenerated in this way were placed in the same tube as in Example 6 and swept with a stream of crude F32 containing, on average, 2375 ppm of F31 at a flow rate of 3.6 l/h and at 80° C.

As shown by the results in the following table, the break-through point appeared after 65 hours' operation in these conditions, which corresponds to a capacity of 4.18% relative to the weight of sieve introduced.

| Cumulative operating period (hours) | Initial F31 content (ppm) | Residual F31 content (ppm) |
|---|---|---|
| 6 | 2160 | <1 |
| 22 | 2200 | <1 |
| 30 | 2350 | <1 |
| 46 | 2450 | <1 |
| 61 | 2550 | <1 |
| 65 | 2580 | 2 |
| 68 | 2600 | 17 |

EXAMPLE 15

A sample of 100 g of Union Carbide 13X sieve was treated for 2 hours at 60° C. with 400 ml of an aqueous solution containing 60 g of potassium nitrate. After draining and rinsing with three 400-ml portions of distilled water, the sieve was dried at 120° C. for 2 hours and then heated to 450° C. for one hour.

34.5 g of the sieve treated in this way were next activated at 250° C. in vacuum (133 Pa) and were then placed in the same tube as in Example 6, which was heated to a temperature of 100° C. and were swept with a stream of crude F32 containing, on average, 2840 ppm of F31, at a flow rate of 3.65 l/h.

Inspection of the results listed together in the following table shows that the break-through point occurred after 76 hours' operation, which corresponds to a treatment capacity of 4.5 g of F31 per 100 g of 13X sieve in the potassium form.

| Cumulative operating period (hours) | Residual F31 content (ppm) |
| --- | --- |
| 6.5 | 0 |
| 22 | 0 |
| 46 | 0 |
| 70 | 0 |
| 76 | ≦1 |

EXAMPLE 16

35.1 g of Union Carbide 13X sieve, activated at 250° C. in vacuum (133 Pa), were placed in the same tube as in Example 6, and then swept with a stream of crude F32 containing, on average, 1865 ppm of F31 and under the autogenous pressure of the F32, that is 12 to 14 bars absolute, depending on the ambient temperature conditions prevailing during the test, the sieve bed being maintained at a temperature of 100° C. The gases were decompressed on leaving the purifier tube and their flow rate was controlled at 3.45 l/h under standard conditions of temperature and pressure.

The break-through point appeared after 79 hours' operation, which corresponds to a capacity of 4.34% relative to the weight of sieve introduced.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Process for the purification of a difluoromethane (F32) containing traces of chlorofluoromethane (F31), comprising passing a gaseous stream of the F32 to be purified over a 13X molecular sieve at a temperature of at least 60° C.

2. Process according to claim 1, wherein the operation is carried out at a temperature of higher than 75° C.

3. Process according to claim 1 wherein the hourly space velocity of the gaseous stream of F32 is between 20 and 2400 $h^{-1}$.

4. Process according to claim 1 wherein, after use, the 13X sieve is regenerated by washing by means of a solution of sodium or potassium carbonate and heating to high temperature under inert atmosphere or in vacuum.

5. Process according to claim 4, wherein, before washing, the sieve is desorbed at 150°–250° C. under a stream of nitrogen or in vacuum.

6. Process according to claim 4 or wherein, after washing the sieve is heated to a temperature of between 200° and 250° C.

7. Process according to claim 3, wherein hourly space velocity is between 40 and 250 $h^{-1}$.

* * * * *